United States Patent [19]
Kaiser et al.

[11] Patent Number: 4,719,223
[45] Date of Patent: Jan. 12, 1988

[54] IMIDAZOLETHIOL DOPAMINE-BETA-HYDROXYLASE INHIBITORS

[75] Inventors: Carl Kaiser, Haddon Heights; Lawrence I. Kruse, Haddonfield, both of N.J.; Stephen T. Ross, Berwyn, Pa.

[73] Assignee: SmithKline Beckman Corporation, Philadelphia, Pa.

[21] Appl. No.: 793,512

[22] Filed: Oct. 31, 1985

[51] Int. Cl.$^4$ .................. A61K 31/415; C07D 233/42
[52] U.S. Cl. ..................................... 514/392; 514/398; 548/317; 548/321; 548/337
[58] Field of Search ................. 548/317, 321, 337; 514/392, 398

[56] References Cited

U.S. PATENT DOCUMENTS

| | | | |
|---|---|---|---|
| 2,180,772 | 11/1939 | Scherer | 568/425 |
| 3,488,423 | 1/1970 | Doebel et al. | 514/392 |
| 3,915,980 | 10/1975 | Gebert et al. | 548/337 |
| 4,340,738 | 7/1982 | Sipido | 548/317 X |
| 4,487,761 | 12/1984 | Cole et al. | 546/296 X |
| 4,532,331 | 7/1985 | Frazee et al. | 548/342 |

FOREIGN PATENT DOCUMENTS

| | | | |
|---|---|---|---|
| 951 | 3/1979 | European Pat. Off. | 548/335 |
| 125033 | 11/1984 | European Pat. Off. | 548/337 |
| 2756639 | 6/1978 | Fed. Rep. of Germany | 548/353 |
| 1155580 | 6/1969 | United Kingdom | 514/392 |
| 2096987 | 10/1982 | United Kingdom | 548/335 |

OTHER PUBLICATIONS

J. Topliss, *J. Med. Chem.*, 1972, 15(10), 1006–1010.
P. Iverson, et al., *Acta Cem. Scand.*, 21:279–285, (1967).
R. Fuller, et al., *Adv. Enzyme Regul.*, 15:267–281, (1976).
C. Runti, et al., *Il Farmaco Ed. Sc.*, 36:260–268, (1980).
Goldstein, *Pharmacol. Rev.*, 18:77–82, (1966).
V. Gebert, et al., *Chemical Abstracts*, 72:39275e, (1970), [*Z. Physiol. Chem.*, 1969, 350(11), 1327–30].
H. Hidaka, et al., *Mol. Pharmacol.*, 9:172–177, (1973).

*Primary Examiner*—Richard A. Schwartz
*Attorney, Agent, or Firm*—Vincent L. Fabiano; Stuart R. Suter; Alan D. Lourie

[57] ABSTRACT

Potent dopamine-β-hydroxylase inhibitors having the Formula:

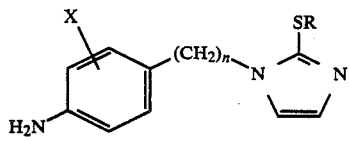

which are useful to inhibit dopamine-β-hydroxylase activity, pharmaceutical compositions including these inhibitors, and methods of using these inhibitors to inhibit dopamine-β-hydroxylase activity in mammals. Also disclosed are novel intermediates useful in preparing the presently invented inhibitors.

13 Claims, No Drawings

IMIDAZOLETHIOL DOPAMINE-BETA-HYDROXYLASE INHIBITORS

FIELD OF THE INVENTION

This invention relates to novel compounds that inhibit dopamine-β-hydroxylase.

BACKGROUND OF THE INVENTION

In the catecholamine biosynthetic pathway, tyrosine is converted in three steps to norepinephrine (NE). Intermediates are dihydroxyphenylalanine (DOPA) and dopamine (DA). Dopamine is hydroxylated to norepinephrine by dopamine-β-hydroxylase (DBH) in the presence of oxygen and ascorbic acid.

Inhibition of catecholamine activity decreases blood pressure. Weinshilboum, *Mayo Clin. Proc.* 55, 39 (1980), reviews compounds that inhibit catecholamine activity by acting upon adrenergic receptors. Alternatively, the catecholamine biosynthetic pathway can be suppressed at any of the three steps, resulting in reduced NE levels. In addition to producing an antihypertensive effect, inhibitors of NE synthesis are active as diuretics, natriuretics, cardiotonics, and vasodilators. Inhibition of DBH activity can have the added advantage of increasing DA levels, which as reported by Ehrreich et al., "New Antihypertensive Drugs," Spectrum Publishing, 1976, pp. 409–432, has selective vasodilator activity at certain concentrations.

DBH inhibitors also have been shown to reduce or prevent formation of gastric ulcers in rats by Hidaka et al., "Catecholamine and Stress," edit. by Usdin et al., Permagon Press, Oxford, 1976, pp. 159–165 and by Osumi et al., *Japan J. Pharmacol.* 23, 904 (1973).

A number of DBH inhibitors are known. These generally are divided into two classes, namely, metal chelating agents, which bind to copper in the enzyme, and phenethylamine analogues. Rosenberg et al., "Essays in Neurochemistry and Neuropharmacology," Vol. 4, edit. by Youdim et al., John Wiley & Sons, 1980, pp. 179–192, and Goldstein, *Pharmacol. Rev.* 18(1), 77 (1966), review DBH inhibitors. The former report that many potent DBH inhibitors have a hydrophobic side chain of size comparable to the aromatic ring of DA, leading the authors to suggest that incorporation of a terminal hydroxyl group on a 4- to 6- carbon side chain on a phenethylamine analogue may yield potent inhibitors.

Known DBH inhibitors include:

(a) 5-alkylpicolinic acids [See, Suda et al., *Chem. Pharm. Bull.* 17, 2377 (1969); Umezawa et al., *Biochem. Pharmacol.* 19, 35 (1969); Hidaka et al., *Mol. Pharmacol.* 9, 172 (1973); Miyano et al., *Chem. Pharm. Bull.* 26, 2328 (1978); Miyano et al., *Heterocycles* 14, 755 (1980); Claxton et al., *Eur. J. Pharmacol.* 37, 179 (1976)];

(b) BRL 8242 [See, Claxton et al., *Eur J. Pharmacol.* 37, 179 (1976)];

(c) 1-alkylimidazole-2-thiols [See, Hanlon et al., *Life Sci.* 12, 417 (1973); Fuller et al., *Adv. Enzyme Regul.* 15, 267 (1976)];

(d) substituted thioureas [See, Johnson et al., *J. Pharmacol. Exp. Ther.* 168, 229 (1969)]; and (e) benzyloxyamine and benzylhydrazine [See, Creveling et al., *Biochim. Biophys. Acta* 64, 125 (1962); Creveling et al., *Biochim. Biophys. Acta* 8, 215 (1962); Van Der Schoot et al., *J. Pharmacol. Exp. Ther.* 141, 74 (1963); Bloom, *Ann. N.Y. Acad. Sci* 107, 878 (1963)].

All the above compounds except benzyloxyamine and benzylhydrazine apparently owe their inhibitory effect to metal chelating properties. Alkyl derivatives of imidazole-2-thiol are more potent, presumably due to non-specific interaction of the alkyl substituent with the enzyme. Benzyloxyamine and benzylhydrazine are phenethylamine analogues which apparently act as competitive inhibitors.

In addition to the above compounds, Runti et al., *Il Farmaco Ed. Sci.* 36, 260 (1980), report that other fusaric acid derivatives and analogues inhibit DBH. These include phenylpicolinic acid, which has twice the inhibitory activity of fusaric acid, and 5-(4-chlorobutyl)picolinic acid, and others such as substituted amides of fusaric acid and acids and amides of 5-butyroylpicolinic acid, 5-aminopicolinic acid and 5-hydrazinopicolinic acid, and derivatives thereof.

Hidaka et al., *Molecular Pharmacology*, 9, 172–177 (1972) report that 5-(3,4-dibromobutyl)picolinic acid and 5-(dimethyldithiocarbamoyl)methylpicolinic acid are DBH inhibitors.

Bupicomide, 5-(n-butyl)picolinamine, is reported by Ehrreich et al., "New Antihypertensive Drugs", Spectrum Publications, 1976, pg. 409–432, to be a DBH inhibitor that has antihypertensive activity.

In European Patent Application No. 125,033 (published Nov. 14, 1984) a series of 1-phenyl and 1-phenylalkylimidazole compounds having a mercapto or alkylthio group in the 2-position are disclosed. These compounds are described as having DBH inhibiting activity.

U.S. Pat. No. 4,487,761 describes several methylpyridine derivatives isolated from the fermentation broth of a strain of Streptoverticillium. These compounds inhibit DBH activity.

U.S. Pat. No. 4,532,331 describes various 1-benzyl-2-aminomethyl imidazole derivatives that inhibit DBH activity and includes pharmaceutical compositions containing these derivatives and methods of using these derivatives to inhibit DBH activity.

Friedman et al., *Psychosomatic Med.* 40, 107 (1978), report that patients treated with alpha-methyl-DOPA, guanethidine, and reserpine, but not propanolol and diuretics, have lowered DBH levels, although the significance of the observation is uncertain.

Non-specific, often toxic effects of known DBH inhibitors have obviated clinical use of these compounds. Fusaric acid, for example, is hepatotoxic. See, for example, Teresawa et al., *Japan. Cir. J.* 35, 339 (1971) and references cited therein. Presumably, the picolinic acid structure interacts with a number of metalloproteins and enzymes non-specifically to produce the observed side effects.

In U.K. Patent Specification No. 1,155,580 are disclosed compounds having the formula:

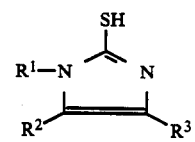

in which $R^2$ and $R^3$ can be H, and $R^1$ can be substituted phenyl. The compounds are said to have analgesic, anti-inflammatory and antipyretic properties. Gerbert et al., U.S. Pat. No. 3,915,980, disclose such compounds wherein R[1] can be phenyl or phen(C$_{1-3}$)alkyl, as intermediates to imidazolyl-2-thioalkanoic acid esters.

Iverson, *Acta Chem. Scand.* 21, 279 (1967) reports compounds having the formula:

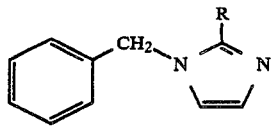

wherein R can be —CO$_2$H or —CH$_2$NHC$_6$H$_5$, but does not report pharmaceutical uses for the compounds.

SUMMARY OF THE INVENTION

The present invention resides in the discovery that DBH is inhibited by substituted-1-(4'-aminoaralkyl)imidazole-2-thiol and substituted-1-(4'-aminoaralkyl)-2-alkylthioimidazole compounds. These compounds are potent and produce prolonged DBH inhibition.

Presently preferred compounds of the invention include:
1-(4'-amino-3',5'-difluorobenzyl)imidazole-2-thiol; and
1-(4'-amino-3',5'-dichlorobenzyl)imidazole-2-thiol.

In a further aspect of the invention there are provided novel intermediates useful in preparing substituted-1-(4'-aminoaralkyl)imidazole-2-thiol and substituted-1-(4'-aminoaralkyl)-2-alkylthioimidazole compounds. Each of the intermediates is a substituted N-acetylaniline also substituted at the 4-position.

The invention also is a method of inhibiting DBH activity in mammals, including humans, which comprises administering internally to a subject an effective amount of a substituted-1-(4'-aminoaralkyl)imidazole-2-thiol or a substituted-1-(4'-aminoaralkyl)-2-alkylthioimidazole compound.

Included in the present invention are pharmaceutical compositions comprising compounds useful in the method of the invention and a pharmaceutical carrier.

DETAILED DESCRIPTION OF THE INVENTION

The presently invented compounds that inhibit DBH have the following formula:

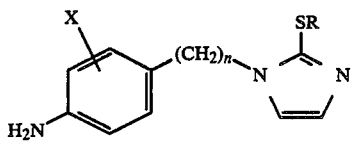

in which:
X is hydrogen, bromo, chloro, fluoro, iodo or any combination thereof up to four substituents;
n is 0–5; and
R is hydrogen or C$_{1-4}$ alkyl; or a pharmaceutically acceptable salt or hydrate thereof.

It is intended that Formula I include the tautomer of the compounds in which R is hydrogen, that is, compounds having the above formula wherein the imidazole moiety has either of the below formulae:

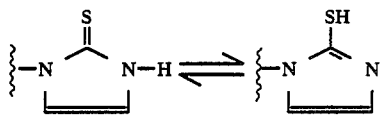

The compounds of Formula I are prepared from corresponding substituted-4-cyanoanilines by known processes such as shown in Scheme I, below. The starting substituted-4-cyanoanilines are known and described in published references and can be obtained readily. Additionally, starting substituted-4-cyanoanilines are preparable from analogous substituted anilines. The substituted anilines are treated with N-bromosuccinimide in a suitable dipolar, aprotic solvent, such as dimethylformamide, by the procedure of Mitchell, et al., *J. Org. Chem.*, 44, 4733 (1979) to prepare substitued-4-bromoanilines. Thereafter the 4-bromo compounds are treated with cuprous cyanide in a suitable dipolar, aprotic solvent, such as dimethylformamide, by the procedure of Friedman and Schechter, *J. Org. Chem.*, 26, 2522 (1961) to yield the desired substituted-4-cyanoaniline compounds.

Scheme I illustrates reaction of substituted-4-cyanoanilines (A) having X substituents that are the same as X in Formula I with an acylating agent such as trifluoroacetic anhydride to produce the corresponding substituted 4-acetamidocyanobenzene (B) followed by reduction by, for example, treatment with a suitable hydrogenation catalyst such as Raney nickel and an organic acid such as formic acid to yield substituted 4-acetamidobenzaldehydes (C). Upon reaction with an aminoacetaldehyde acetal, such as aminoacetaldehyde dimethylacetal, followed by reduction by, for example, by treatment with a strong reducing agent such as NaBH$_4$ and an inorganic acid such as hydrochloric acid, the 4-acetamidobenzaldehydes (C) yield substituted 4-acetamidobenzylaminoacetaldehyde acetal hydrochlorides (E). Thereafter, substituted-1-(4'-aminoaralkyl)imidazole-2-thiols (F) are prepared by reacting the 4-acetamidobenzylaminoacetaldehyde acetal hydrochlorides (E) with potassium thiocyanate in the presence of a strong inorganic acid such as hydrochloric acid.

SCHEME I

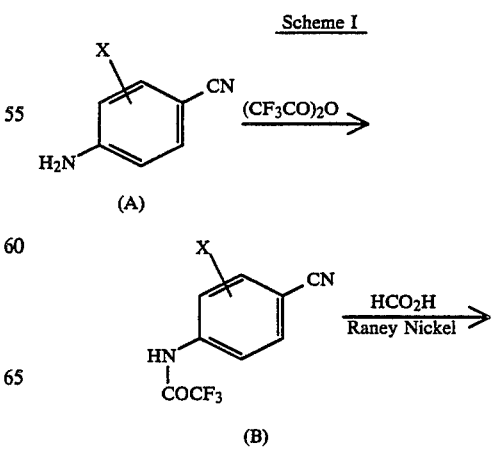

-continued
Scheme I

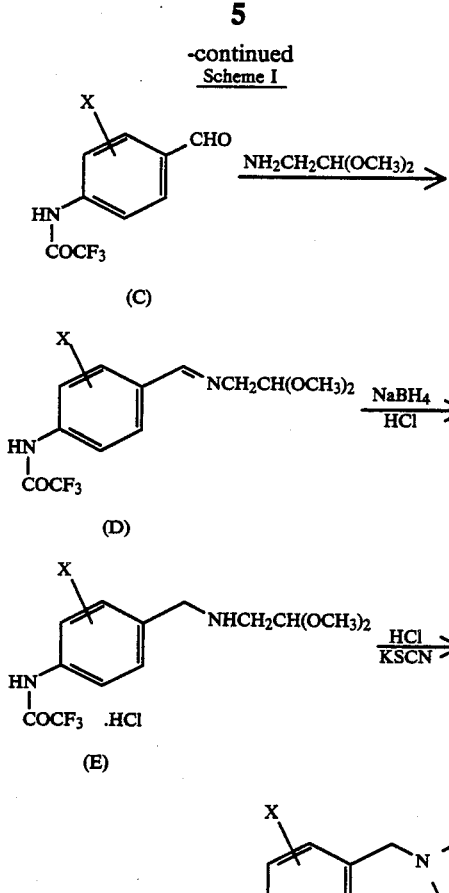

As illustrated in Scheme I, n is 1, however n can be from 0 to 5. The compounds wherein n is 2, 3, 4, or 5 preferably are prepared as described in Example 4, below. In the synthesis of these compounds, the process of Scheme I is employed except that the substituted-4-cyanoanilines are replaced by substituted-4-aminophenylalkylnitriles such as substituted-4-aminobenzylnitriles, substituted-4-aminophenethylnitriles, substituted-4-aminophenylpropylnitriles, and substituted-4-aminophenylbutylnitriles.

The 1-(4'-amino substituted phenyl)imidazole-2-thiols (n is 0) preferably are prepared by reaction of an appropriately substituted, optionally protected, 4-aminophenylisothiocyanate with an aminoacetaldehyde acetal followed by strong acid catalyzed cyclization, as illustrated in Example 3, below.

The compounds wherein R is a methyl group are prepared by alkylating corresponding 1-(4'-aminoaralkyl)imidazole-2-thiols with methyl iodide in methanol by known procedures. Other alkyl halides such as methyl bromide or methyl chloride can be substituted in an appropriate solvent for methyl iodide. Further, the compounds where R is an alkyl group other than methyl are prepared by reacting the corresponding substituted-1-(4'-aminoaralkyl)imidazole-2-thiol with an alkyl halide, such as butyl iodide, to yield the desired substituted-1-(4'-aminoaralkyl)-2-alkylthioimidazole compound of the invention.

In preparing substituted-1(4'-aminoaralkyl)imidazole-2-thiols, novel intermediate compounds of the following formula are synthesized:

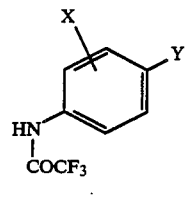

in which:
X is H, Br, Cl, F, I or any combination thereof of up to four substituents:
Y is CN, CHO,

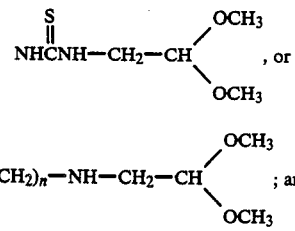

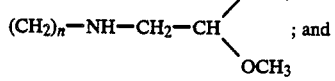

n is 1-5;
except compounds in which:
X is four H's; and
Y is CN or CHO.

The pharmaceutically acceptable acid addition salts of the compounds of the invention are formed with strong or moderately strong organic or inorganic acids by methods known in the art. For example, the base is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Because the compounds of Formula I inhibit DBH activity, they have therapeutic value as diuretic, natriuretic, cardiotonic, antihypertensive and vasodilator agents, as well as antiulcerogenic and anti-Parkinsonian agents. Listed in Table I are the compounds of the invention that were tested for in vitro DBH inhibition by a standard procedure for assaying conversion of tyramine to octopamine in the presence of DBH. J. J. Pisano, et al., Biochim. Biophys. Acta; 43, 566–682 (1960). Octopamine was assayed following sodium periodate oxidation to p-hydroxybenzaldehyde by measuring spectrophotometric absorbance at 330 nm. In Table I, inhibition is given in molar concentration of compound at which DBH activity was halved ($IC_{50}$). Melting points (mp) are given in °C. Fusaric acid, by this test was found to have an $IC_{50}$ of $8 \times 10^{-7}$M.

TABLE I

| Compound | mp | $IC_{50}$ |
|---|---|---|
| 1-(4'-amino-3',5'-dichlorobenzyl)-imidazole-2-thiol | 233–236° | $3.1 \times 10^{-6}$ |
| 1-(4'-amino-3',5'-difluorobenzyl)-imidazole-2-thiol | 181–184° | $1.2 \times 10^{-6}$ |

One of the compounds of the invention was tested for its effect in vivo on peripheral dopamine (DA) and norepinephrine (NE) levels substantially by the procedure of DaPrada and Zurcher, *Life Sciences*, 19, 1161, (1976). Groups of five spontaneously hypertensive rats were dosed orally, twice, the second dose approximately 18 hours after the first, and were sacrificed about 2 hours after the second dose. Averaged results, expressed in micrograms of DA and NE per gram of tissue are given in Table II.

TABLE II

| Compound | DA (μg/g) | NE (μg/g) | DA/NE Ratio |
|---|---|---|---|
| Control (Saline) | 0.229 | 6.43 | 0.0358 |
| Fusaric Acid 50 mg/kg | 0.529 (1) | 5.63 | 0.0937 (1) |
| 1-(4'-amino-3',5'-difluorobenzyl)-imidazole-2-thiol 50 mg/kg | 0.821 (1) | 5.53 | 0.151 (1) |

(1) p < 0.001

Further, spontaneously hypertensive rats were dosed with a suspension or solution of 1-(4'-amino-3',5'-difluorobenzyl)imidazole-2-thiol at a dose of 50 mg/kg intraperitoneally, and mean arterial blood pressure was monitored for 260 minutes using indwelling cannulae positioned in the tail arteries. Approximate forty percent reductions in blood pressure were observed fifteen minutes following administration of this compound. At 260 minutes after administration of this compound, blood pressure remained reduced by approximately ten percent when compared to vehicle-treated controls.

The finding that the substituted-1-(4'-aminoalkyl)-imidazole-2-thiol compounds possess efficacy as DBH inhibitors was unexpected based upon testing of several related compounds. This testing was performed using compounds prepared by substituting various phenolic isosteres for the phenolic hydroxy group of another DBH inhibitor, 1-(3',5'-difluoro-4'-hydroxybenzyl-)imidazole-2-thiol (U.S. patent application Ser. No. 590,665, filed Mar. 19, 1984). Compounds wherein the phenolic hydroxy group was replaced by —NHCHO, —NHCOCF$_3$, —NHSO$_2$NH$_2$, and —CH$_2$SO$_2$CH$_3$ were tested in vitro and found to be devoid of DBH inhibiting activity. In contrast, as can be seen from Table I, the IC$_{50}$ of 1-(4'-amino-3',5'-difluorobenzyl-)imidazole-2-thiol compares very favorably with that of 1-(3',5'-difluoro-4'-hydroxybenzyl)imidazole-2-thiol which is 8×10$^{-8}$M.

The compounds of Formula I are incorporated into convenient dosage forms such as capsules, tablets or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating and compressing, when necessary, for tablet forms, or mixing, filling and dissolving the ingredients, as appropriate, to give the desired oral or parenteral products.

Doses of the present compounds in a pharmaceutical dosage unit will be an efficacious, nontoxic quantity selected from the range of 0.1-100 mg/kg of active compound, preferably 0.1-50 mg/kg. The selected dose is administered to a human patient in need of DBH inhibition from 1-6 times daily, orally, rectally, by injection, or continuously by infusion. Dosage units for oral administration to humans preferably contain from 1 to 500 mg. of active compound. Parenteral administration, which uses lower dosages, is preferred. Oral administration, at higher dosages, however, also can be used when safe and convenient for the patient.

The following examples are illustrative of preparation of Formula I compounds. The examples are not intended to limit the scope of the invention as defined above and as claimed below.

EXAMPLE 1

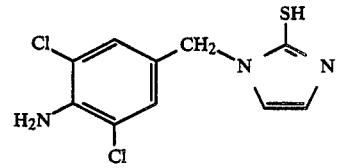

(i) Preparation of N-trifluoroacetyl-4-cyano-2,6-dichloroaniline

Twenty-five grams (0.1337 mole) of 4-cyano-2,6-dichloroaniline was dissolved in 250 ml of methylene chloride, and 30.9 g (20.8 ml, 0.1471 mole) of trifluoroacetic anhydride was added slowly with stirring. The solution was allowed to stand overnight and then was neutralized by the addition of 5% aqueous sodium carbonate, precipitating a white crystalline solid which was filtered and dried to give 28.0 g (74% yield) of N-trifluoroacetyl-4-cyano-2,6-dichloroaniline, m.p.: 134°–136° C.

(ii) Preparation of 4-trifluoroacetamido-3,5-dichlorobenzaldehyde

Twenty-seven grams (0.0954 mole) of the above N-trifluoroacetylcyanoaniline was dissolved in 270 ml 88% formic acid and 27 g of Raney nickel was added. The mixture was stirred and heated at reflux for 1.5 hours. The reaction mixture was cooled, filtered, and the filtrate diluted with water, and the mixture was extracted three times with methylene chloride. The combined extracts were back-extracted with 5% aqueous sodium bicarbonate and the methylene chloride solution was then concentrated to give a yellow oil. This was taken up in ether and hexane (1:1 to 1:2) added until cloudiness developed. Chilling the mixture caused a crystalline solid to form which was filtered and dried to give 18.85 g (69% yield) of 4-trifluoroacetamide-3,5-dichlorobenzaldehyde, m.p.: 88°–90° C.

(iii) Preparation of 1-(4'-amino-3',5'-dichlorobenzyl)imidazole-2-thiol

Five grams (0.0175 mole) of the above benzaldehyde was dissolved in 50 ml methanol and 1.84 g (0.0175 mole) of aminoacetaldehyde dimethyl acetal was added. This solution was refluxed for one hour, chilled, and 0.68 g (0.0175 mole) sodium borohydride was added in small portions with stirring. The mixture then was refluxed for a few minutes, cooled, and diluted with water, and extracted three times with ether. The combined ether extracts were concentrated under vacuum to give a yellow oil. This oil was stirred with 25 ml of water, 12 ml of ethanol, and 6 ml of 12N (aqueous) hydrochloric acid, and 2.04 g (0.0210 mole) potassium thiocyanate was added. The mixture was stirred and refluxed for 30 minutes, and then cooled and diluted with water which caused a precipitate to form. This was filtered and dried to give 6.7 g of solid. This solid was triturated with water and then with methanol to give 5.7 g of solid after drying. This was taken up in 25 ml of 2.5N (aqueous) sodium hydroxide, and the solution was refluxed one hour, cooled, and neutralized to pH 7 with dilute (aqueous) hydrochloric acid. A yellow solid precipitated which was filtered and dried to give 3.63 g, m.p.: 223°–230° C. dec. This was recrystallized from dimethylformamideacetonitrile to give 1.18 g (24% yield) of 1-(4'-amino-3',5'-dichlorobenzyl)imidazole-2-thiol, m.p.: 233°–236° dec.

EXAMPLE 2

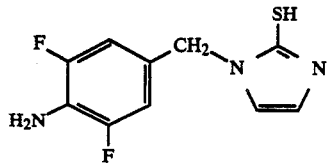

(i) Preparation of 1-(4'-amino-3',5'-difluorobenzyl)imidazole-2-thiol-4-bromo-2,6-difluoroaniline Fifty grams (0.39 mole) of 2,6-difluoroaniline was treated with 71.0 g (0.39 mole) of N-bromosuccinimide in 250 ml of dimethylformamide by the procedure of Mitchell, Lai and Williams, *J. Org. Chem.*, 44, 4733 (1979) to give a total yield of 50.2 g (62%) of 4-bromo-2,6-difluoroaniline, m.p.: 64°–66° C.

(ii) Preparation of 4-cyano-2,6-difluoraniline

A 22.6 g quantity (0.11 mole) of the above bromo compound was treated with 11.7 g (0.13 mole) cuprous cyanide in 17 ml dimethylformamide by the method of Friedman and Schechter, *J. Org. Chem.*, 26, 2522 (1961), and employing the ethylenediamine-sodium cyanide complex-decomposition procedure in this reference [25 ml ethylenediamine and 20 ml 10% aqueous sodium cyanide] to give 4.3 g (26%) of 4-cyano-2,6-difluoroaniline, crystallized from ether-hexane, m.p.: 110°–111° C. (soften 107° C.).

(iii) Preparation of N-trifluoroacetyl-4-cyano-2,6-difluoraniline

A 4.07 g quantity (0.026 mole) of the above cyanoaniline was dissolved in 50 ml methylene chloride, and 10 ml of trifluoroacetic anhydride was added with stirring. The solution spontaneously warmed to reflux and reflux was continued for a few minutes on a steam bath. The solution was cooled and treated with 5% (aqueous) sodium carbonate to precipitate a reddish-white solid. This was filtered and washed with hexane and water. The aqueous portion of the filtrate was neutralized to pH 7 with 3N (aqueous) hydrochloric acid. A white solid precipitated which was filtered and dried and was N-trifluoroacetyl-4-cyano-2,6-difluoroaniline, m.p.: 133.5°–135° C., total yield 6.15 g (93%).

(iv) Preparation of 3,5-difluoro-4-trifluoroacetamidobenzaldehyde

A 5.78 g (0.023 mole) quantity of the above trifluoroacetyl compound was dissolved in 60 ml of 88% formic acid and 6.0 g of Raney nickel was added. This mixture was stirred at reflux for 1.5 hours and was cooled and filtered. The filtrate was diluted with water and extracted three times with methylene chloride. The combined extracts were back-extracted with 5% (aqueous) sodium bicarbonate, and were concentrated to give a solid residue which was recrystallized from ether-hexane to give 4.45 g (76% yield) of 3,5-difluoro-4-trifluoroacetamidobenzaldehyde, m.p.: 122°–125° C.

(v) Preparation of N-(3,5-difluoro-4-trifluoroacetamidobenzyl)aminoacetaldehyde dimethylacetal hydrochloride A 4.3 g quantity (0.017 mole) of the above benzaldehyde was dissolved in 22 ml of 95% ethanol, and 1.79 g (0.017 mole) of aminoacetaldehyde dimethyl acetal was added. The solution was stirred at reflux for one hour, cooled and 0.64 g (0.017 mole) of sodium borohydride was added in several small portions. The reaction mixture then was heated to reflux for a few minutes, cooled, and diluted with water. The pH was adjusted to seven and the mixture was extracted three times with ether. The combined ether extracts were concentrated to give an oil which was redissolved in ether and the solution was carefully treated with ethereal hydrogen chloride to give a white crystalline solid, 4.4 g. The pH of the aqueous phase was adjusted to 8.2, and the mixture was re-extracted three times with ether. Concentration of the combined extracts yielded an oil which was converted to a solid hydrochloride salt as described above, 0.45 g. Total yield of N-(3,5-difluoro-4-trifluoroacetamidobenzyl)aminoacetaldehyde dimethyl acetal hydrochloride was 4.85 g (83%), m.p.: decomposes above 120° C.

(vi) Preparation of 1-(4'-amino-3',5'-difluorobenzyl)imidazole-2-thiol

A 4.4 g quantity (0.012 mole) of the above N-benzylaminoacetal hydrochloride was dissolved in 22 ml water, and 1.13 g (0.012 mole) potassium thiocyanate was added followed by 5.5 ml 12N (aqueous) hydrochloric acid. The solution was stirred and heated to 90° C. at which point an oil separated. The mixture was stirred and refluxed for 30 minutes without further obvious change, then cooled and allowed to stand. The oil solidified and was filtered. This was taken up in 25 ml of 2N (aqueous) sodium hydroxide. The mixture was heated at reflux for one hour, and the solution then was cooled and neutralized to pH 7, depositing a yellow solid, 2.2 g, on drying. This was dissolved in 10–20 ml of methanol, and the solid reprecipitated by adding 20–50 ml of ether. The solid then was recrystallized from ethyl acetate to give 1.0 g (36% yield) of 1-(4'-amino-3',5'-difluorobenzyl)imidazole-2-thiol, m.p.: 181°–184° C.

Treatment of 1-(4'-amino-3',5'-difluorobenzyl)imidazole-2-thiol in ethanolic solution with a solution of hydrogen chloride in diethyl ether yields 1-(4'-amino-3',5'-difluorobenzyl)imidazole-2-thiol dihydrochloide.

EXAMPLE 3

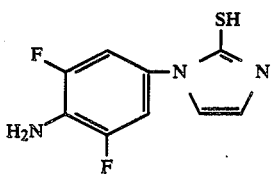

A solution of 4-amino-3,5-difluorophenyl isothiocyanate in trichloromethane is treated with an equimolar amount of aminoacetaldehyde dimethyl acetal. The solvent is evaporated, and the residue is recrystallized from ethanol to yield N-(4-amino-3,5-difluorophenyl)-N'-(β,β-dimethoxyethyl)thiourea. A suspension of this thiourea in concentrated sulfuric acid and water (1:4) was refluxed for three hours. The mixture then is cooled and the solid that forms is filtered, washed with water, and dried. Recrystallization from ethanol yields 1-(4'-amino-3',5'-difluorophenyl)imidazole-2-thiol.

EXAMPLE 4

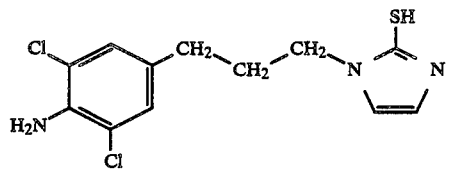

The process of Example 1 using 4-amino-3,5-dichlorophenylpropylnitrile in place of 4-cyano-2,6,-dichloroaniline yields 1-(4'-amino-3',5'-dichlorophenylpropyl)imidazole-2-thiol.

EXAMPLE 5

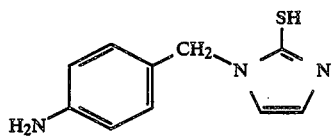

The process of Example 2 using 4-cyanoaniline in place of 4-amino-2,6-dichloroaniline yields 1-(4'-aminobenzyl)imidazole-2-thiol.

EXAMPLE 6

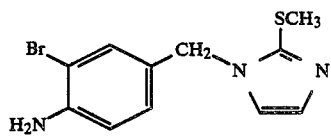

Reaction of 1-(4'-amino-3'-bromobenzyl)imidazole-2-thiol, prepared as in Example 1 using 2-bromoaniline in place of 2,6-difluoroaniline, with methyl iodide and sodium methoxide in methanol by known techniques yields 1-(4'-amino-3'-bromobenzyl)-2-methylthioimidazole.

EXAMPLE 7

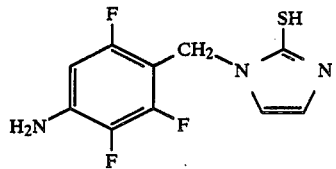

The process of Example 2 using 2,3,5-trifluoroaniline in place of 2,6-difluoraniline yields 1-(4'-amino-2',3',6'-trifluorobenzyl)imidazole-2-thiol.

EXAMPLE 8

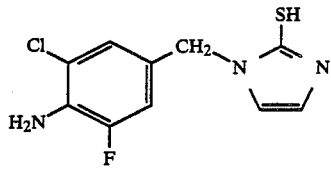

The process of Example 2 using 2-chloro-6-fluoroaniline in place of 2,6-difluoroaniline yields 1-(4'-amino-3'-chloro-5'-fluorobenzyl)imidazole-2-thiol.

EXAMPLE 9

An oral dosage form for administering the presently invented compounds is produced by screening, mixing, and filling into a hard gelatin capsule the ingredients in Table III, below.

TABLE III

| Ingredients | Amounts |
| --- | --- |
| 1-(4'-amino-3',5'-difluorobenzyl)-imidazole-2-thiol | 50 mg |
| magnesium stearate | 5 mg |
| lactose | 75 mg |

EXAMPLE 10

The sucrose, calcium sulfate dihydrate and substituted-1-(4'-aminoaralkyl)imidazole-2-thiol shown in Table IV below, are mixed and granulated with a 10% gelatin solution. The wet graules are screened, dried, mixed with the starch, talc and stearic acid, screened and compressed into a tablet.

TABLE IV

| Ingredients | Amounts |
| --- | --- |
| 1-(4'-amino-3',5'-dichlorobenzyl)-imidazole-2-thiol | 100 mg |
| calcium sulfate dihydrate | 150 mg |
| sucrose | 20 mg |
| starch | 10 mg |
| talc | 5 mg |
| stearic acid | 3 mg |

EXAMPLE 11

1-(4'-amino-3'-bromobenzyl)imidazole-2-thiol, 75 mg, is dispersed in 25 ml of normal saline to prepare an injectable preparation.

While the preferred embodiments of the invention are illustrated by the above, it is to be understood that the invention is not limited to the precise instructions herein

What is claimed is:

1. A compound of the Formula:

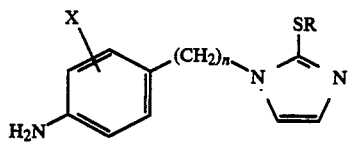

in which:
X is hydrogen, bromo, chloro, fluoro, iodo or any combination thereof of up to four substituents;
n is 0–5; and
R is hydrogen or $C_{1-4}$ alkyl; or a pharmaceutically acceptable salt or hydrate thereof.

2. A compound of claim 1 in which R is hydrogen.
3. A compound of claim 2 in which n is 1.
4. A compound of claim 3 that is 1-(4'-amino-3',5'-diclorobenzyl)imidazole-2-thiol.
5. A compound of claim 3 that is 1-(4'-amino-3',5'-dichlorobenzyl)imidazole-2-thiol.
6. A pharmaceutical composition for inhibiting dopamine-β-hydroxylase activity, comprising a pharmaceutically acceptable carrier and an amount sufficient to produce said inhibition of a compound of claim 1.
7. A pharmaceutical composition of claim 6 in which the compound is 1-(4'-amino-3',5'-difluorobenzyl)imidazole-2-thiol.
8. A pharmaceutical composition of claim 6 in which the compound is 1-(4'-amino-3',5'-dichlorobenzyl)imidazole-2-thiol.
9. A pharmaceutical composition of claim 6 containing from 1 to 500 mg of compound.
10. A method of inhibiting dopamine-β-hydroxylase activity in mammals which comprises:
administering internally to a subject in need of such inhibition an effective amount of a compound of claim 1.
11. A method of claim 10 in which the compound is 1-(4'-amino-3',5'-difluorobenzyl)imidazole-2-thiol.
12. A method of claim 10 in which the compound is 1-(4'-amino-3',5'-dichlorobenzyl)imidazole-2-thiol.
13. A method of claim 10 that comprises administering an amount selected from the range of 0.1 to 100 mg per kilogram of compound.

* * * * *